US012025499B2

(12) United States Patent
De Geus et al.

(10) Patent No.: US 12,025,499 B2
(45) Date of Patent: Jul. 2, 2024

(54) APPARATUS AND METHOD FOR DETERMINING A PROPERTY OF PRODUCTS

(71) Applicant: Aweta G&P B.V., Pijnacker (NL)

(72) Inventors: Johannes Cornelis De Geus, Nootdorp (NL); Valéry Jean Georges Quenon, Nootdorp (NL)

(73) Assignee: AWETA G&P B.V., Pijnacker (NL)

( * ) Notice: Subject to any disclaimer, the term of this patent is extended or adjusted under 35 U.S.C. 154(b) by 78 days.

(21) Appl. No.: 17/616,794

(22) PCT Filed: Jun. 5, 2020

(86) PCT No.: PCT/NL2020/050367
§ 371 (c)(1),
(2) Date: Dec. 6, 2021

(87) PCT Pub. No.: WO2020/246888
PCT Pub. Date: Dec. 10, 2020

(65) Prior Publication Data
US 2022/0307905 A1 Sep. 29, 2022

(30) Foreign Application Priority Data

Jun. 6, 2019 (NL) ..................................... 2023271

(51) Int. Cl.
*G01J 3/42* (2006.01)
*G01J 3/02* (2006.01)
(Continued)

(52) U.S. Cl.
CPC ............... *G01J 3/42* (2013.01); *G01J 3/0202* (2013.01); *G01J 3/0218* (2013.01);
(Continued)

(58) Field of Classification Search
CPC .......... G01J 3/42; G01J 3/0202; G01J 3/0218; G01J 3/0289; G01J 3/10; G01J 2003/102;
(Continued)

(56) References Cited

U.S. PATENT DOCUMENTS 5,164,795 A 11/1992 Conway
5,675,419 A 10/1997 Van Den Bergh et al.
(Continued)

FOREIGN PATENT DOCUMENTS

WO WO-2019043231 A1 * 3/2019 ............. B07C 5/342
WO WO-2019177468 A1 * 9/2019 ............. G01N 21/84

OTHER PUBLICATIONS

International Search Report for PCT/NL2020/050367 dated Aug. 21, 2020.
(Continued)

*Primary Examiner* — Michelle M Iacoletti
*Assistant Examiner* — Noah J. Haney
(74) *Attorney, Agent, or Firm* — Stephen J. Weyer, Esq.; Stiles & Harbison, PLLC

(57) ABSTRACT

Apparatus for determining a property of products, in particular plant or animal products, the apparatus comprising: a conveyor configured for conveying products one-by-one along a transport path in a transport direction; a light source configured for illuminating a first illumination area of the transport path, wherein the first illumination area extends substantially across the transverse width of the transport path; and a sensor structure configured for receiving light from a sensing area of the transport path, wherein the sensing area extends substantially across the transverse width of the transport path, wherein the sensing area is adjacent to the first illumination area.

23 Claims, 5 Drawing Sheets

(51) Int. Cl.
*G01J 3/10* (2006.01)
*G01N 21/84* (2006.01)
*G01N 33/02* (2006.01)
*G01N 21/31* (2006.01)
*G01N 21/85* (2006.01)

(52) U.S. Cl.
CPC ............... *G01J 3/0289* (2013.01); *G01J 3/10* (2013.01); *G01J 2003/102* (2013.01); *G01N 21/31* (2013.01); *G01N 21/84* (2013.01); *G01N 2021/845* (2013.01); *G01N 2021/8466* (2013.01); *G01N 2021/8592* (2013.01); *G01N 33/025* (2013.01); *G01N 2201/0833* (2013.01)

(58) Field of Classification Search
CPC ...... G01N 21/31; G01N 21/84; G01N 33/025; G01N 2021/845; G01N 2021/8466; G01N 2201/0833; G01N 2021/8592
USPC .......................................................... 356/319
See application file for complete search history.

(56) References Cited

U.S. PATENT DOCUMENTS

| | | | |
|---|---|---|---|
| 6,094,265 A | 7/2000 | Ishikawa et al. | |
| 6,410,872 B2* | 6/2002 | Campbell | G01N 21/85 |
| | | | 209/580 |
| 6,512,577 B1 | 1/2003 | Ozanich | |
| 7,103,207 B2* | 9/2006 | Brown | G01N 21/3563 |
| | | | 382/141 |
| 7,173,708 B2* | 2/2007 | Ibarra | B07C 5/3422 |
| | | | 250/341.8 |
| 7,316,322 B2* | 1/2008 | Kawabata | G01N 21/359 |
| | | | 209/509 |
| 9,351,498 B2* | 5/2016 | Grimm | G01N 21/94 |
| 9,670,006 B2* | 6/2017 | Ruigrok | B65G 47/24 |
| 9,910,024 B2* | 3/2018 | Burgstaller | B07C 5/3422 |
| 10,197,504 B2* | 2/2019 | Sahu | B07C 5/3422 |
| 10,458,965 B1* | 10/2019 | Iyer | G01N 21/251 |
| 10,888,902 B2* | 1/2021 | Balthasar | B07C 5/342 |
| 10,908,076 B2 | 2/2021 | Thienpont et al. | |
| 11,079,334 B2* | 8/2021 | Furihata | G06T 7/0008 |
| 11,249,030 B2* | 2/2022 | Van Olmen | G01N 21/255 |
| 2002/0008055 A1 | 1/2002 | Campbell et al. | |
| 2003/0149544 A1 | 8/2003 | Brown et al. | |
| 2003/0156281 A1 | 8/2003 | Crezee et al. | |
| 2005/0226466 A1 | 10/2005 | Seymour | |
| 2006/0118726 A1 | 6/2006 | Kawabata et al. | |
| 2009/0080706 A1 | 3/2009 | Tao et al. | |
| 2012/0250025 A1 | 10/2012 | Moshe et al. | |
| 2016/0252461 A1* | 9/2016 | Balthasar | G01N 21/85 |
| | | | 356/445 |
| 2018/0143073 A1* | 5/2018 | Goldring | G01J 3/42 |
| 2019/0086325 A1 | 3/2019 | Thienpont et al. | |

OTHER PUBLICATIONS

International Preliminary Report on Patentability for PCT/NL2020/050367 dated Sep. 20, 2021.

Third Party Observation for related application EP 20200731997 dated Jan. 18, 2024.

Kaur, et al, "Comparison of hand-held near infrared spectrophotometers for fruit dry matter assessment", 2017, pp. 267-277, vo. 25, No. 4, Journal of Near Infrared Spectroscopy.

Greensill, et al, "A remote acceptance probe and illumination configuration for spectral assessment of internal attributes of intact fruit", 2000, pp. 1674-1684, vol. 11, Meas. Sci. Technol.

* cited by examiner

APPARATUS AND METHOD FOR DETERMINING A PROPERTY OF PRODUCTS

The present invention concerns an apparatus and a method for determining a property, for example a quality related property, of products, in particular plant or animal products. The result of the determining may be used, for example, for sorting the products according to their respective determined property, for example to separate low-quality products from high-quality products.

Such an apparatus is known from practice. The known apparatus comprises: a conveyor configured for conveying products one-by-one along a transport path in a transport direction; a light source configured for illuminating an illumination area, for example a ring-shaped illumination area, of the transport path; and a sensor structure configured for receiving light from a sensing area, for example a circular area, of the transport path, wherein the illumination area may surround the sensing area. For example, U.S. Pat. No. 6,512,577B1 discloses such an apparatus.

In the known apparatus, light from the light source may travel into the product, illuminating the interior of the product, whereafter at least some of the light may leave the product, where it may be received by the sensor structure. Since the received light has interacted with the interior of the product, it may be analyzed or processed to determine a property of the product, in particular a property relating to an internal quality of the product. Such an approach can be particularly useful for detecting internal quality parameters of plant products and/or animal products, which may be at least somewhat translucent. For example, in the case of fruit products, bruises or other faults may thus be detected in the product.

It is generally required that the products be positioned precisely with respect to the light source and the sensor structure to ensure a proper optical interaction between the light source, the product and the sensor structure. However, in some scenarios, it may be difficult or undesired to control the position of the products so precisely. This may be the case, for example, when products of different shapes and/or sizes are processed together at a substantially high rate, e.g. in the same production line. In such a production line, for example, a transverse width (measured transverse to a transport direction) of a conveyor may be adapted to accommodate a product of a maximum size, e.g. a maximum width, which is generally larger size than a size of other products in the same line. As a result, the transverse position of products may vary from product to product, e.g. due to variations in shapes and size.

An additional challenge may arise with elongated products such as pears, because their shapes can be more irregular and their sizes can vary more from one product to another. This can complicate their positioning on some conveyors, for example endless roller conveyors with diabolo-shaped rollers.

It is therefore an object of the invention to provide an improved apparatus and method, in particular a solution for reliably and quickly determining a property of products, in particular plant or animal products, wherein shapes, sizes and positions, in particular transverse positions, of the products may vary among the products, preferably at high processing rates.

To that aim, according to the invention, there is provided an apparatus for determining a property of products, in particular plant or animal products, the apparatus comprising:

a conveyor configured for conveying products one-by-one along a transport path in a transport direction;

a light source configured for illuminating a first illumination area of the transport path, wherein the first illumination area extends substantially across the transverse width of the transport path; and a sensor structure configured for receiving light from a sensing area of the transport path, wherein the sensing area extends substantially across the transverse width of the transport path, wherein the sensing area is adjacent to the first illumination area.

During use, products may be passed near, e.g. under the light source and the sensor structure to be internally illuminated by the light source, wherein light from the light source may enter the product and be scattered in the product, whereafter at least some of the scattered light may leave the product (at the sensing area) and be received by the sensor structure. Thus, using the apparatus, light which has travelled into the product and has been scattered may be detected. Preferably, other illumination light, which is e.g. reflected by the product, is substantially prevented from being received by the sensor structure.

With such an apparatus, properties of products can be determined reliably and quickly, providing a high throughput of products, substantially irrespective of variations in shapes, sizes and positions, particularly transverse positions, of the products. In particular, properties of elongated products can thus be determined reliably, wherein the elongated products are preferably positioned on the conveyor such that they extend substantially in a transverse direction to the transport direction. The determined properties may advantageously be used for sorting the products according to their respective determined properties. Thus, the invention also enables reliable and efficient sorting of products according to determined properties of the products.

Preferably, the light source and the sensor structure are positioned above and preferably spaced apart from the conveyor, so that contamination, e.g. from dirty products, of the light source and/or sensor structure may be reduced, thus further improving reliability.

The light source may be configured to apply an illumination beam having a substantially elongated cross section, for example a rectangular cross-section, an oval cross-section, or the like, but that is not required. The optical axis of the beam may extend substantially perpendicularly to the transport direction and/or may be substantially parallel to a viewing direction of the sensor structure. Preferably, the optical axis of the beam and the viewing direction of the sensor structure together enclose an angle, for example in the range of 0 to 30 degrees, for example in the range of 5 to 20 degrees. Such a configuration can help to prevent that light is reflected from the product's surface into the sensor structure, in particular for substantially convex products and/or convex product parts.

The invention further provides a method for determining a property of products, in particular plant or animal products, the method comprising: passing products to be measured one-by-one along a transport path in a transport direction;

illuminating at least a first illumination area and preferably a second illumination area of the transport path, wherein the illumination area extends substantially across the transverse width of the transport path;

receiving light from a sensing area of the transport path, wherein the sensing area extends substantially across the transverse width of the transport path, wherein the sensing area is adjacent to the first illumination area and preferably adjacent to the second illumination area; and processing the received light, in particular to determine a property of each of the subsequent products.

Such a method provides the above mentioned advantages.

Further advantageous elaborations of the invention are provided by the features of the dependent claims.

The invention will be explained further with reference to exemplary embodiments and drawings. In the drawings.

Figure 1:
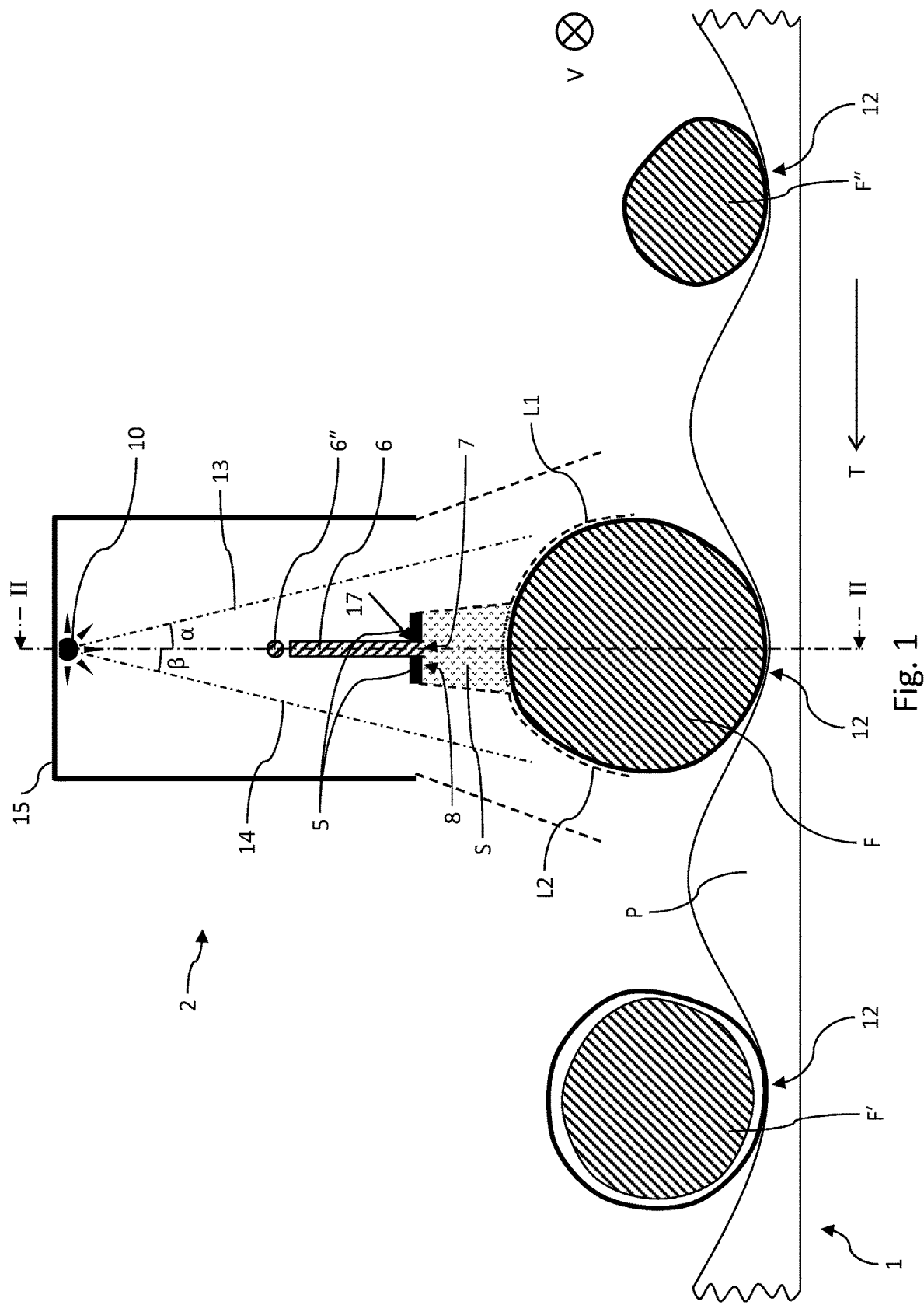
FIG. 1 shows a schematic side view of an apparatus of an exemplary embodiment along the line I-I in FIG. 3.

In the drawings, corresponding or similar features are indicated with corresponding or similar reference signs.

In the exemplary embodiment, an apparatus for determining a property of products F, F', F" comprises a conveyor 1 configured for conveying products F, F', F" one-by-one along a transport path P in a transport direction T.

The products F, F', F" may be of varying shapes and sizes. In particular, the products F, F', F" can be plant or animal products. Preferably, the products F, F', F" are at least partially translucent, i.e. light may travel into and out of the products, and preferably the product's interior F, F', F" acts as a scattering medium, i.e. light traveling into them may be deflected or diffused. For example, the products F, F', F" may be fruit products F, F', F". It will be appreciated that the invention may be carried out with other types of products.

The exemplary apparatus further comprises a light source 2 which is configured for illuminating a first illumination area L1 of the transport path P (for illuminating the products passing that area), wherein the first illumination area L1 extends substantially across the transverse width W of the transport path P.

The exemplary apparatus further comprises a sensor structure 3 configured for receiving light from a sensing area S of the transport path P, wherein the sensing area S extends substantially across the transverse width W of the transport path P, wherein the sensing area S is adjacent to the first illumination area L1.

As shown, the sensor structure 3 and preferably the light source 2 are preferably positioned above the conveyor 1 and preferably substantially spaced apart from the conveyor 1 (and the product transport path P), so that a risk of contamination of the light source 2 and/or the sensor structure, e.g. from dirty products, is reduced, thus improving reliability of the apparatus.

The sensing area S is preferably a substantially linear area, wherein the sensing area S preferably extends in a transverse direction V to the transport direction T.

In this example, the light source 2 is configured to apply a first illumination beam having a substantially rectangular cross section. The optical axis 13 of the first beam may extend substantially perpendicularly to the transport direction T and/or may be substantially parallel to a viewing direction of the sensor structure 3, wherein the viewing direction may be a direction in which a fiber optic cable end 7 extends. Preferably, the optical axis 13 of the first beam and the viewing direction of the sensor structure together enclose an angle α, for example in the range of 0 to 30 degrees, for example in the range of 5 to 20 degrees. Such a configuration can help to prevent that light is reflected from the product's surface into the sensor structure 3, in particular for substantially convex products F, F', F", and/or convex product parts.

Such a sensing area can advantageously extend along an elongated product which is passed by the conveyor, in particular when the elongated product is positioned on the conveyor such that it extends substantially in the transverse direction V. Thus, properties of such products may be determined efficiently and reliably.

Figure 2:
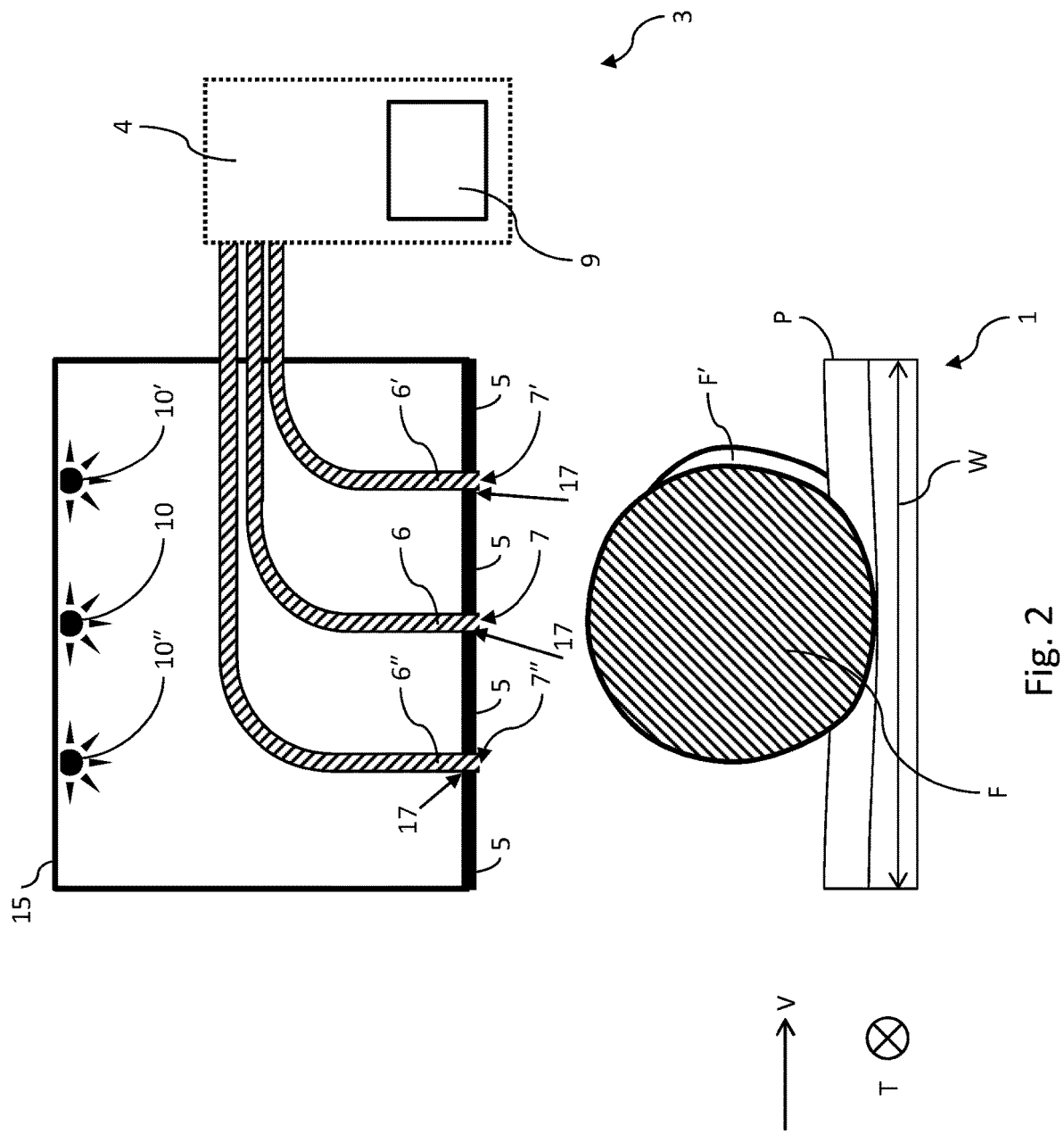
FIG. 2 shows a schematic cross section of the apparatus of FIG. 1 along the line II-II in FIG. 1.
Figure 3:
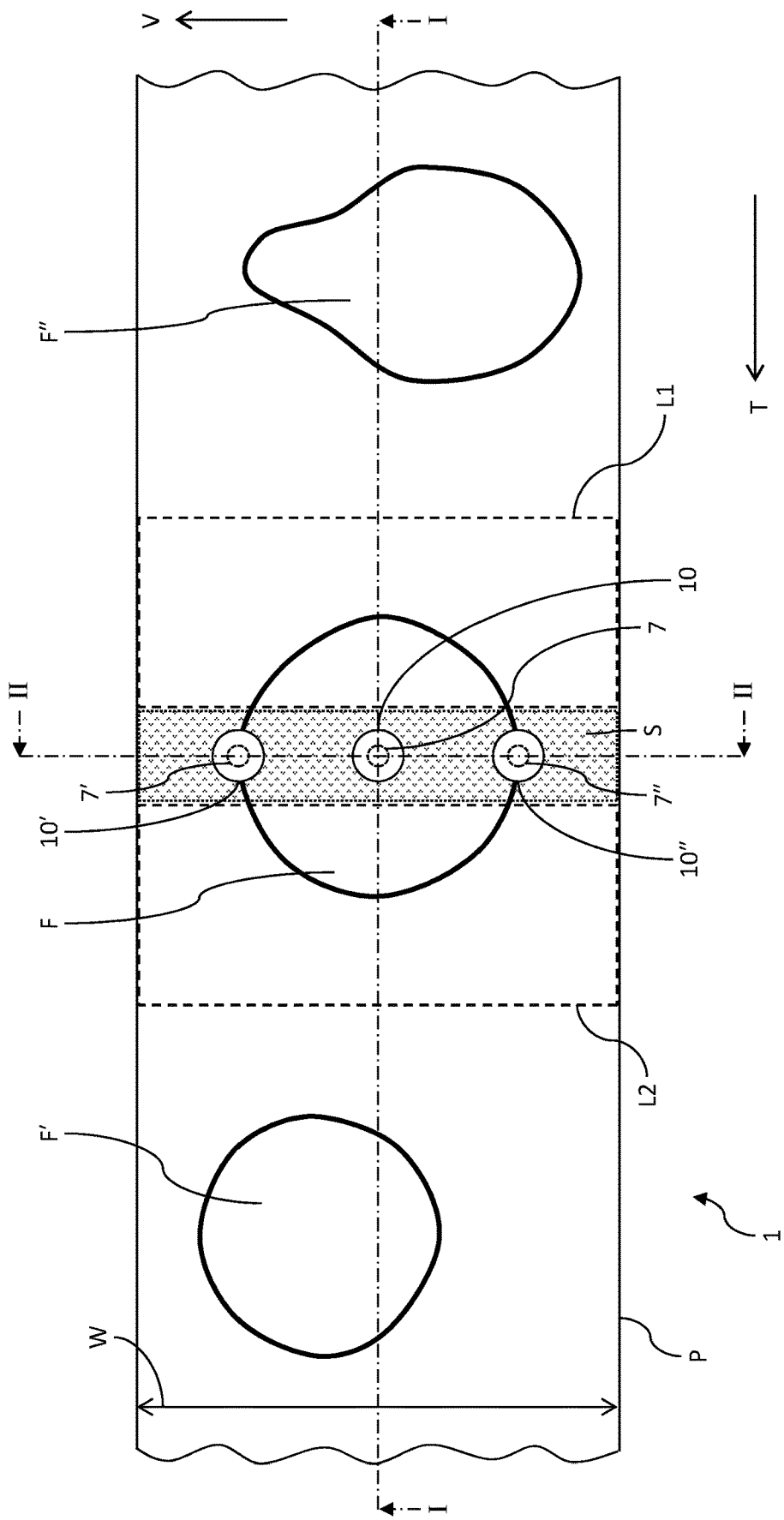
FIG. 3 shows a schematic top-down opened view of the apparatus of the exemplary embodiment of FIG. 1.

In a preferred embodiment, as shown in FIGS. 1-3, the light source 2 is further configured for illuminating a second illumination area L2 that is spaced-apart from the first area L1, viewed along the transport path P, wherein the sensing area S is preferably positioned between the first and second illumination areas L1, L2.

Such a configuration can provide improved performance as the product may be illuminated substantially more homogeneously with respect to the sensing area.

If the light source 2 is thus configured for illuminating the second illumination area L2, the light source 2 is preferably configured to apply a second illumination beam having (in this case) a substantially rectangular cross section. The optical axis 14 of the second beam may extend substantially perpendicularly to the transport direction T and/or may be substantially parallel to a viewing direction of the sensor structure 3, wherein the viewing direction may be a direction in which a fiber optic cable end 7 extends. Preferably, the optical axis 14 of the second beam and the viewing direction of the sensor structure together enclose an angle β, for example in the range of 0 to 30 degrees, for example in the range of 5 to 20 degrees. Such a configuration can help to prevent that light is reflected from the product's surface into the sensor structure 3, in particular for substantially convex products F, F', F", and/or convex product parts.

It will be appreciated that in some embodiments the light source 2 may be configured such that only a first illumination area L1 is illuminated.

The light source 2 may be configured in various different ways using various types of light emitters and optical components.

The light source 2 is preferably configured to emit light, preferably including multiple wavelengths, towards the illumination area (L1, L2). For example, the light source 2 may include at least a first halogen lamp 10 for illuminating the illumination area L1, L2.

The various wavelengths of light may be especially suitable for penetrating the products for example at respective various depths from the product's surface, enabling potential distinctions in the received light between interactions of shallower and deeper structures. Such a light source also advantageously enables more reliable analysis of the received light, e.g. using spectrometry to analyze a difference in wavelength spectrum between light emitted by the light source and light received by the sensor structure.

The light source 2 may include an array of light emitting members 10, 10', 10", e.g. lamps, preferably halogen lamps 10, 10', 10", wherein the light emitting members 10, 10', 10" are preferably distributed substantially evenly across the transverse width W of the transport path P, wherein the light emitting members 10, 10', 10" are preferably positioned substantially along a transverse direction V to the transport direction T.

Such an array provides simple and effective means for illuminating a substantially linear illumination area substantially homogeneously.

Figure 5:
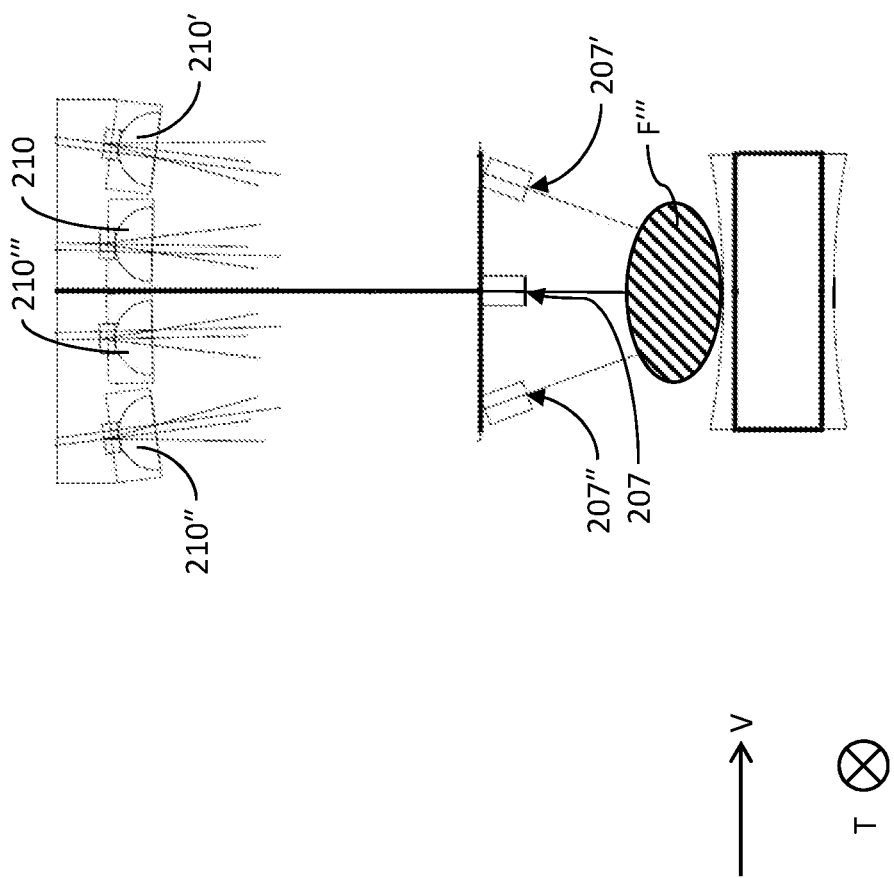
FIG. 5 is similar to FIG. 2, showing a schematic cross section of part of a further embodiment of the apparatus.

In some embodiments, as shown in FIG. 5, the light emitting members 210, 210', 210", 210'" may be directed substantially towards a common position along the transverse direction V. Such a configuration may enable improved illumination of a product F'".

In a preferred embodiment, the light source 2 includes a light blocking shield 5 for defining the illumination beams, i.e. for blocking part of the light emitted by the light emitting member 10, 10', 10". Preferably (as in the drawings) each light emitting member 10, 10', 10" of the light source 2 is positioned above the light blocking shield 5.

Such a shield may help to prevent that light from the light emitting member is reflected towards a light sensitive part of the sensor structure, e.g. by an outer surface of a product. Such reflected light could otherwise complicate or inhibit a reliable detection and/or analysis of light which has travelled through the product from the first and/or second illumination area.

Preferably, see e.g. the present example, the shield 5 extends transverse to the transport path P and has (small) apertures 17 for light passage to/of the sensor structure 3. As follows from the drawings, an inner side of the shield 5 may face the light emitting members 10, 10', 10" of the light source 2. In a preferred embodiment (see FIGS. 1 and 3) the shield 5 can effect a elongated shield shadow (line shadow) that provides the sensing area S that is viewed by sensor structure 3.

In the present example, the apparatus further includes a housing 15, which may be configured to block a further part of the light emitted by the light emitting member 10, 10', 10", for example to reduce and/or block an illumination of surroundings of the apparatus, wherein the surroundings may include further products F', F" which are respectively downstream and upstream of the product F, for example.

The sensor structure 3 preferably includes at least a first fiber optic cable 6 having a light receptive cable end 7 which is directed towards the sensing area S (the cable end 7 extending through the shield 5, as follows from the drawings). For example, a number of fiber optic cables 6 having light receptive cable ends 7 may be provided, e.g. one, two, three (as in the present example, or more.

Such a fiber optic cable provides simple and effective means for receiving and conducting light from the sensing area towards an area where the light may be processed, e.g. a spectrometer.

The cable end 7 may be positioned at a side 8 of the shield 5 which is faced towards the sensing area S, wherein the fiber optic cable 6 preferably traverses the shield 5. The cable end 7 is preferably directed away from the light source 2, preferably directed substantially radially outwardly from the light source 2. A field of view (viewing direction) of the cable end 7 is preferably such, that it is limited to the sensing area S. The cable end 7 preferably includes a collimator (not shown), for example a lens, for controlling a field of view of the cable end 7.

This configuration can advantageously prevent that light other than that emitted from the sensing area S is received by the sensing structure 3, so that a property of the products can be determined more reliably.

The sensor structure 3 may include a processor 4 (schematically indicated in FIG. 2) for processing the received light, in particular for determining a property of each of the subsequent products F, F', F'". The processor preferably includes a sensor 9, for example a spectrometer 9, for measuring a spectral property, which may be indicative of a chemical composition of the product, e.g. a concentration of sugar and/or acidity.

Thus, such a processor may enable reliable and efficient analysis of the received light for determining a property of the products. Moreover, such automated processing enables further automated actions downstream of the apparatus, so that for example products may be sorted automatically according to their respective determined property.

In a preferred embodiment, the sensor structure 3 includes an array of fiber optic cables 6, 6', 6", wherein the respective cable ends 7, 7', 7" are preferably distributed substantially evenly (symmetrically) across the transverse width W of the transport path P, wherein the cable ends 7, 7', 7" are preferably positioned substantially along a transverse direction V to the transport direction T. Alternatively, the respective cable ends 7, 7', 7" can be distributed unevenly (asymmetrically) across the transverse width W of the transport path P.

Such an array-like configuration can enable that light is received substantially evenly from substantially the entire sensing area, improving reliability of the receiving and/or the determining.

In some embodiments, as shown in FIG. 2, the cable ends 7, 7', 7" are directed substantially parallel with respect to each other, whereas in other embodiments, as shown in FIG. 5, the cable ends 207, 207', 207" may be directed differently, e.g. towards a common position along the transverse direction V. Such a configuration as shown in FIG. 5 may enable more reliable receiving and/or determining.

In such an embodiment, the sensor structure 3 may be configured to combine, e.g. add, light received by at least two, preferably all, of the fiber optic cables 6, 6', 6" of the array of fiber optic cables 6, 6', 6", so that a single sensor, e.g. a spectrometer, may process the received light using only a single fiber optic connector. Alternatively, the sensor structure 3 may be configured to process light received by at least one, for example each of the cables 6, 6', 6" separately, wherein the sensor structure 3 may include separate sensors (not shown) for separate cables 6, 6', 6".

Figure 4:
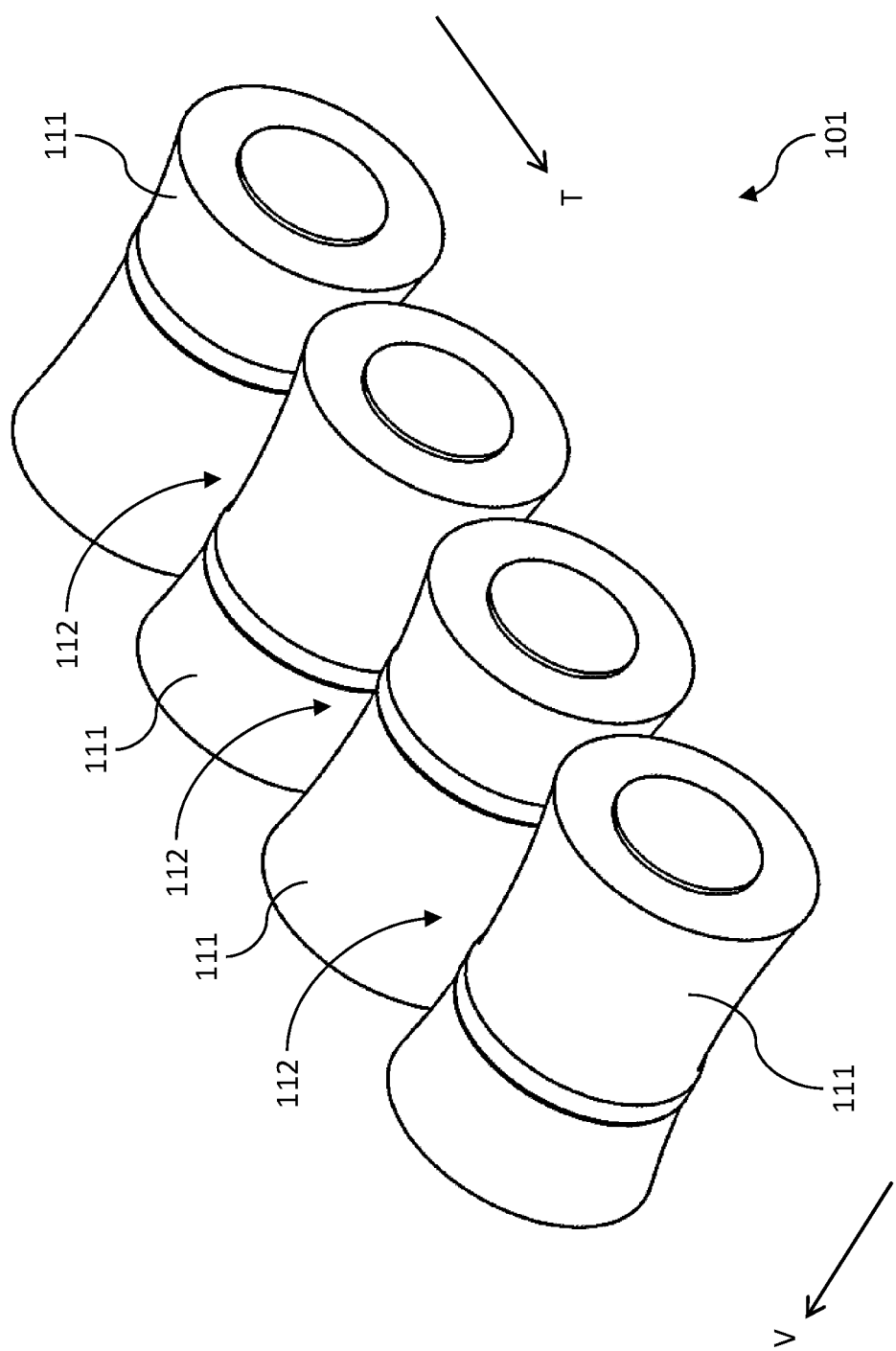
FIG. 4 shows a perspective view of an endless roller conveyor, including diabolo-shaped rollers, of a further embodiment.

FIG. 4 shows part of a further embodiment of the conveyor 101 of the apparatus. As shown in FIG. 4, the conveyor 101 may be an endless roller conveyor 101, preferably including diabolo-shaped rollers 111, wherein the conveyor 101 is preferably configured to receive products F, F', F" in nests 112 which are formed by adjacent rollers 111.

Such a conveyor is particularly suitable for conveying elongated products of varying shapes and sizes safely and efficiently.

Thus, there is provided an apparatus and method for reliably and quickly determining a property of products, in particular plant or animal products, wherein shapes, sizes and positions, in particular transverse positions, of the products may vary among the products.

While the invention has been explained using exemplary embodiments, it will be appreciated that the invention may be carried out using variations and alternatives that fall within the scope of the claims, as will be clear to the skilled person.

For example, the light source may include at least one laser, light emitting diode, halogen lamp, and/or other light emitting means and may be configured to emit light of various wavelengths including invisible light, e.g. infrared and/or ultraviolet.

The term 'light' is not limited to wavelengths which are visible to the human eye. The apparatus, for example the light source and/or the sensor structure, may further include various optical components such as lenses, mirrors, filters, apertures, collimators, etc. to direct and/or otherwise condition the light.

The sensor structure, in particular the sensor and/or the processor may include various optical sensors and/or optical analysis means, such as a photo diode, a camera, an image processor, etc.

Preferably, the illumination area L1, L2 is entirely separate from the sensing area S; alternatively, there can be some overlap in these areas.

An array of light emitting members may include any plural number of light emitting members. An array of fiber optic cable may include any plural number of fiber optic cables. The number of fiber optic cables may be a different number from the number of light emitting members.

An afore-mentioned illumination beam may e.g. have a substantially rectangular cross-section, alternatively, it can e.g. have an oval or round cross-sectional shape, or differently.

Further, the first illumination area L1 extends substantially across the transverse width W of the transport path P, however, other areas at or near the transport path P can also be illuminated by the illumination beam (i.e. path illumination by the illumination beam is not restricted to the first illumination area L1).

Even more, a single illumination beam can be applied/used to illuminate both said first and second illumination area L1, L2, see e.g. the embodiment in FIG. 1 in case only a single light source 10 is present, resulting in a single source beam that is split into two subbeams by the shield 5 to illuminate the two illumination areas L1, L2.

LIST OF REFERENCE SIGNS

1. Conveyor
2. Light source
3. Sensor structure
4. Processor
5. Shield
6. First fiber optic cable
6', 6". Further fiber optic cables
7. Light receptive cable end of first cable
7', 7". Light receptive cable ends of further cables
8. Side of shield
9. Sensor
10. First light emitting member
10'-10'". Further light emitting members
11. Diabolo-shaped rollers
12. Nests of conveyor
13. Optical axis of first light beam
14. Optical axis of second light beam
15. Housing
17. Shield aperture
L1. First illumination area
L2. Second illumination area
F. First product
F'-F'". Further products
P. Transport path
S. Sensing area
T. Transport direction
V. Transverse direction
W. Transverse width
α. Angle of optical axis of first light beam
β. Angle of optical axis of second light beam

The invention claimed is:

1. An apparatus for determining a property of products, the apparatus comprising:

a conveyor configured for conveying products one-by-one in a transport direction along a transport path of the conveyor;

a light source configured for illuminating a first illumination area of the transport path in which products are supported by the conveyor, wherein the first illumination area extends substantially across the transverse width of the transport path; and a sensor structure configured for receiving light from a sensing area of the transport path in which products are supported by the conveyor, wherein the sensing area extends substantially across the transverse width of the transport path, wherein the sensing area is adjacent to the first illumination area, wherein the light source is configured to apply a first illumination beam, wherein the optical axis of the first illumination beam and a viewing direction of the sensor structure together enclose an angle in the range of 0 to 30 degrees, and wherein the light source is configured to apply a second illumination beam, wherein the optical axis of the second illumination beam and a viewing direction of the sensor structure together enclose an angle.

2. The apparatus according to claim 1, wherein the sensing area is a substantially linear area, wherein the sensing area extends in a transverse direction to the transport direction.

3. The apparatus according to claim 1, wherein the light source is further configured for illuminating a second illumination area, wherein the sensing area is positioned between the first and second illumination areas.

4. The apparatus according to claim 1, wherein the light source includes a shield for defining the light source's at least one of the first illumination beam and the second beam.

5. The apparatus according to claim 4, wherein a light receptive cable end is positioned at a side of the shield which is faced towards the sensing area, wherein a fiber optic cable traverses the shield, and Wherein the sensor structure includes at least the first fiber optic cable having the light receptive cable end which is directed towards the sensing area.

6. The apparatus according to claim 1, wherein the sensor structure includes at least a first fiber optic cable having alight receptive cable end which is directed towards the sensing area, wherein the light receptive cable end extends through a light blocking shield, wherein a field of view of the light receptive cable end is adapted such that it is limited to the sensing area.

7. The apparatus according to claim 6, wherein the light receptive cable end is directed away from the light source, directed substantially radially outwardly from the light source, wherein the cable end includes a collimator for controlling a field of view of the cable end.

8. The apparatus according to claim 6, wherein the sensor structure includes an array of fiber optic cables, wherein the cable ends of the array of fiber optic cables are positioned substantially along a transverse direction to the transport direction.

9. The apparatus according to claim 8, wherein the sensor structure is configured to combine light received by at least two of the fiber optic cables of the array of fiber optic cables.

10. The apparatus according to claim 1, wherein the sensor structure includes a processor for processing the received light, for determining a property of each of the subsequent products, wherein the processor includes a sensor for measuring a spectral property of the received light.

11. The apparatus according to claim 1, wherein the light source is configured to emit light, including multiple wavelengths, towards the first illumination area.

12. The apparatus according to claim 11, wherein the light source includes at least a first halogen lamp for illuminating the first illumination area.

13. The apparatus according to claim 1, wherein the light source includes an array of light emitting members, wherein the light emitting members are distributed substantially evenly across the transverse width of the transport path.

14. The apparatus according to claim 1, wherein the conveyor is an endless roller conveyor, including diabolo-shaped rollers, wherein the conveyor is configured to receive products in nests which are formed by adjacent rollers.

15. The apparatus according to claim 1, wherein the sensor structure is positioned above the conveyor and substantially spaced apart from the conveyor, wherein light emitting members of the light source are positioned above a light blocking shield to illuminate two separate illumination areas.

16. The apparatus according to claim 1, wherein the light source includes a light blocking shield, configured to split emitted light into two subbeams, to illuminate two separate illumination areas.

17. The apparatus according to claim 16, wherein the light blocking shield extends below light emitting members of the light source.

18. The apparatus according to claim 1, including a light blocking shield for defining the light source's at least one of the first illumination beam and the second illumination beam, wherein the shield extends transverse to the transport path, below light emitting members of the light source, and has apertures for the sensor structure.

19. The apparatus according to claim 1, wherein the optical axis of the first illumination beam and a viewing direction of the sensor structure together enclose an angle in the range of 5 to 20 degrees, and wherein the optical axis of the second illumination beam and a viewing direction of the sensor structure together enclose an angle ($\beta$) in the range of 0 to 30 degrees.

20. The apparatus of claim 1, wherein the light source is configured to apply the second illumination beam, wherein the optical axis of the second illumination beam and a viewing direction of the sensor structure together enclose an angle ($\beta$) in the range of 0 to 30 degrees.

21. The apparatus of claim 1, wherein the products have an elongated shape and are disposed on the conveyor transverse to a conveyor direction.

22. A method for determining a property of products, the method comprising:
    passing products to be measured one-by-one along a transport path in a transport direction in which products are supported by a conveyor;
    illuminating at least a first illumination area and a second illumination area of the transport path in which products are supported by the conveyor, wherein the first illumination area extends substantially across the transverse width of the transport path;
    receiving light from a sensing area of the transport path, wherein the sensing area extends substantially across the transverse width of the transport path in which products are supported by the conveyor, wherein the sensing area is adjacent to the first illumination area and adjacent to the second illumination area, wherein the sensing area is a linear area that is positioned between the first illumination area and the second illumination area; and
    processing the received light to determine a property of each of the subsequent products.

23. A method for sorting products, the method comprising:
    determining a property of each of the products according to claim 22; and
    sorting the products according to their respective determined property.

* * * * *